(12) United States Patent
Hirama

(10) Patent No.: US 8,241,218 B2
(45) Date of Patent: Aug. 14, 2012

(54) ULTRASONIC DIAGNOSTIC APPARATUS

(75) Inventor: Makoto Hirama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 895 days.

(21) Appl. No.: 12/179,093

(22) Filed: Jul. 24, 2008

(65) Prior Publication Data

US 2009/0043209 A1 Feb. 12, 2009

(30) Foreign Application Priority Data

Jul. 27, 2007 (JP) ................................. 2007-196613

(51) Int. Cl.
*A61B 8/14* (2006.01)
(52) U.S. Cl. .............................. 600/459; 73/602; 73/627
(58) Field of Classification Search .................... 73/627, 73/602, 618, 620, 625, 632, 649; 600/459
See application file for complete search history.

(56) References Cited

U.S. PATENT DOCUMENTS

| | | | | | |
|---|---|---|---|---|---|
| 4,417,475 | A | * | 11/1983 | Okazaki ........................... | 73/606 |
| 4,622,978 | A | * | 11/1986 | Matsuo et al. ................ | 600/441 |
| 5,329,929 | A | * | 7/1994 | Sato et al. ....................... | 600/441 |
| 5,562,095 | A | * | 10/1996 | Downey et al. ............... | 600/445 |
| 5,928,151 | A | * | 7/1999 | Hossack et al. ............... | 600/443 |
| 6,080,108 | A | * | 6/2000 | Dunham ........................ | 600/445 |
| 6,116,244 | A | * | 9/2000 | Hossack et al. ............... | 600/441 |
| 6,122,222 | A | * | 9/2000 | Hossack et al. .................... | 367/7 |
| 6,341,174 | B1 | * | 1/2002 | Callahan et al. .............. | 382/154 |
| 6,342,889 | B1 | * | 1/2002 | Callahan ........................ | 345/427 |
| 6,378,376 | B1 | * | 4/2002 | Derman et al. ................. | 73/606 |
| 6,544,186 | B1 | * | 4/2003 | Shelby et al. ................. | 600/463 |
| 6,697,067 | B1 | * | 2/2004 | Callahan et al. .............. | 345/427 |
| 6,755,787 | B2 | * | 6/2004 | Hossack et al. ............... | 600/447 |
| 6,825,838 | B2 | * | 11/2004 | Smith et al. ................... | 345/419 |

(Continued)

FOREIGN PATENT DOCUMENTS

| JP | 60-122548 | 7/1985 |
|---|---|---|
| JP | 6-233765 | 8/1994 |
| JP | 7-236642 | 9/1995 |
| JP | 10-502194 | 2/1998 |

(Continued)

OTHER PUBLICATIONS

Japanese Office Action dated mailed Mar. 27, 2012 for Japanese Patent Application No. 2007-196613 (with English Translation).

*Primary Examiner* — Peter Macchiarolo
*Assistant Examiner* — Samir M Shah
(74) *Attorney, Agent, or Firm* — Oblon, Spivak, McClelland, Maier & Neustadt, L.L.P.

(57) ABSTRACT

A probe includes a transducer unit including a plurality of transducers which are arrayed in the first direction, transmit ultrasonic waves and receive echo signals, and a moving mechanism for continuously moving the transducer unit in the second direction crossing the first direction. A movement control unit controls the moving mechanism to continuously move the transducer unit in the second direction. A transmission unit causes the transducer unit to generate ultrasonic waves. A scan line signal generation unit generates a plurality of actual measurement scan line signals by delaying and adding a plurality of echo signals from the transducer unit. A scan line signal calculation unit calculates a plurality of mathematical scan line signals constituting a plurality of mathematical electronic scan planes from the plurality of actual measurement scan line signals. An image generation unit generates multislice tomograms on the basis of the plurality of calculated mathematical scan line signals.

15 Claims, 6 Drawing Sheets

U.S. PATENT DOCUMENTS

| | | | |
|---|---|---|---|
| 7,171,255 B2 * | 1/2007 | Holupka et al. | 600/427 |
| 7,302,092 B1 * | 11/2007 | Fenster et al. | 382/154 |
| 7,428,334 B2 * | 9/2008 | Schoisswohl et al. | 382/173 |
| 7,668,342 B2 * | 2/2010 | Everett et al. | 382/106 |
| 7,844,320 B2 * | 11/2010 | Shahidi | 600/424 |
| 7,856,130 B2 * | 12/2010 | Suri et al. | 382/128 |
| 2007/0016020 A1 * | 1/2007 | Oshiki et al. | 600/437 |

FOREIGN PATENT DOCUMENTS

| | | |
|---|---|---|
| JP | 10-179576 | 7/1998 |
| JP | 11-9603 | 1/1999 |
| JP | 2000-175914 | 6/2000 |
| JP | 2001-17428 A | 1/2001 |
| JP | 2005-118081 | 5/2005 |
| JP | 2007-21179 | 2/2007 |

* cited by examiner

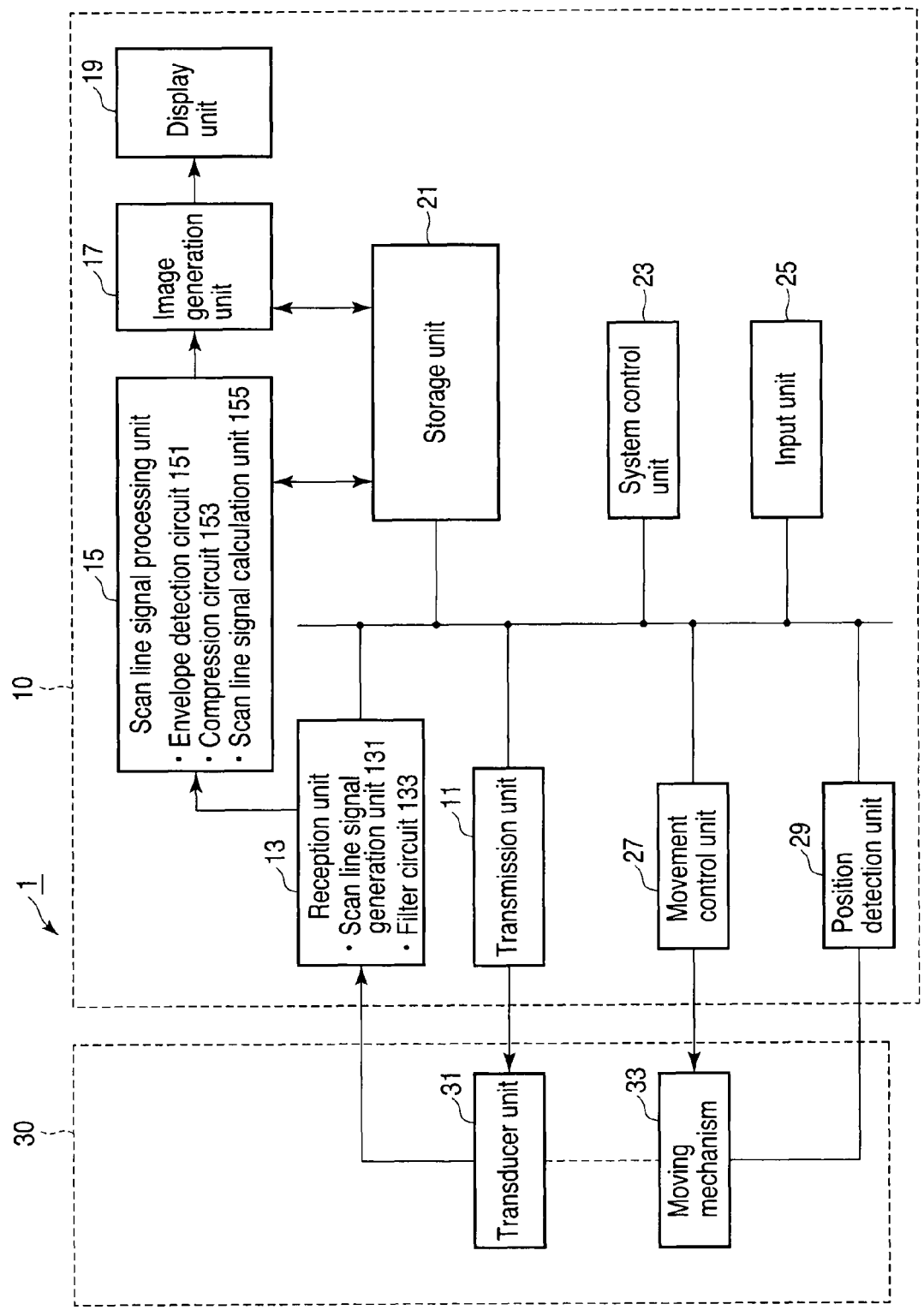
F I G. 1

ULTRASONIC DIAGNOSTIC APPARATUS

CROSS-REFERENCE TO RELATED APPLICATIONS

This application is based upon and claims the benefit of priority from prior Japanese Patent Application No. 2007-196613, filed Jul. 27, 2007, the entire contents of which are incorporated herein by reference.

BACKGROUND OF THE INVENTION

1. Field of the Invention

The present invention relates to an ultrasonic diagnostic apparatus which performs three-dimensional scanning.

2. Description of the Related Art

There is available an ultrasonic diagnostic apparatus which performs electronic scanning while mechanically moving a probe (mechanical scanning) for three-dimensional scanning (see Jpn. Pat. Appln. KOKAI Publication No. 10-179576). Performing electronic scanning while mechanically scanning a probe will be referred to as electronic/mechanical combination scanning. A probe for electronic/mechanical combination scanning has a transducer unit comprising a plurality of transducers arrayed in a line. A transmission unit controls the delay times of driving pulses to the transducer unit so as to sequentially switch ultrasonic scan lines. A delay-and-sum circuit delays and adds a plurality of echo signals received by the transducer unit to convert the signals into actual measurement scan line signals. The ultrasonic diagnostic apparatus generates a plurality of actual measurement scan line signals by mechanically scanning the probe in a direction in which the transducer unit crosses an electronic scan plane (in a direction generally perpendicular to the electronic scan plane) at the time of electronic scanning. Multislice tomograms are generated on the basis of a plurality of actual measurement scan line signals. A pseudo-three-dimensional image is generated by performing rendering processing of a set of generated multislice tomograms.

As an electronic/mechanical combination scanning method, a method of repeating electronic scanning while mechanically and continuously moving a transducer unit is available. In this method, however, an electronic scan plane tilts with respect to the direction of movement. In this case, actual measurement multislice tomograms tilting with respect to the direction of movement are generated on the basis of a plurality of actual measurement scan line signals constituting the electronic scan plane tiling with respect to the direction of movement. A pseudo-three-dimensional image is generated by performing rendering processing of a set of generated actual measurement multislice tomograms. However, this method requires complicated rendering processing, and hence is not practical. In addition, since electronic scan planes in forward and backward paths in mechanical scanning differ from each other, this method requires complicated rendering processing in consideration of the difference.

As shown in FIG. 13, there is available a method of intermittently moving the transducer unit such as moving→stopping→electronic scanning→moving→stopping→electronic scanning in order to make the electronic scan plane perpendicular to the direction of movement. This method, however, requires complicated control of a moving mechanism and of electronic scanning. Furthermore, the method is unsuitable for high-speed 3D scanning because the ultrasonic transducer unit is mechanically stopped.

BRIEF SUMMARY OF THE INVENTION

It is an object of the present invention to provide an ultrasonic diagnostic apparatus which can easily generate high-resolution, high-quality pseudo-three-dimensional images while implementing high-speed 3D scanning which performs electronic scanning while mechanically and continuously moving a transducer unit.

An ultrasonic diagnostic apparatus according to a first aspect of the present invention comprising: probe including a transducer unit including a plurality of transducers which are arrayed in a first direction, transmit ultrasonic waves and receive echo signals, and a moving mechanism for continuously moving the transducer unit in a second direction crossing the first direction; a control unit which controls the moving mechanism to continuously move the transducer unit in the second direction; a transmission unit which causes the transducer unit to generate ultrasonic waves; a signal generation unit which generates a plurality of actual measurement scan line signals by delaying and adding a plurality of echo signals from the transducer unit; a signal calculation unit which calculates a plurality of mathematical scan line signals constituting a plurality of mathematical electronic scan planes from the plurality of actual measurement scan line signals; and an image generation unit which generates multislice tomograms on the basis of the plurality of calculated mathematical scan line signals.

An ultrasonic diagnostic apparatus according to a second aspect of the present invention comprising: a storage unit which stores a plurality of actual measurement scan line signals constituting a plurality of actual measurement electronic scan planes; a signal calculation unit which calculates a plurality of mathematical scan line signals constituting a plurality of mathematical electronic scan planes from the plurality of actual measurement scan line signals; and an image generation unit which generates multislice tomograms on the basis of the plurality of calculated mathematical scan line signals.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an ultrasonic diagnostic apparatus according to an embodiment;

DETAILED DESCRIPTION OF THE INVENTION

Figure 2:
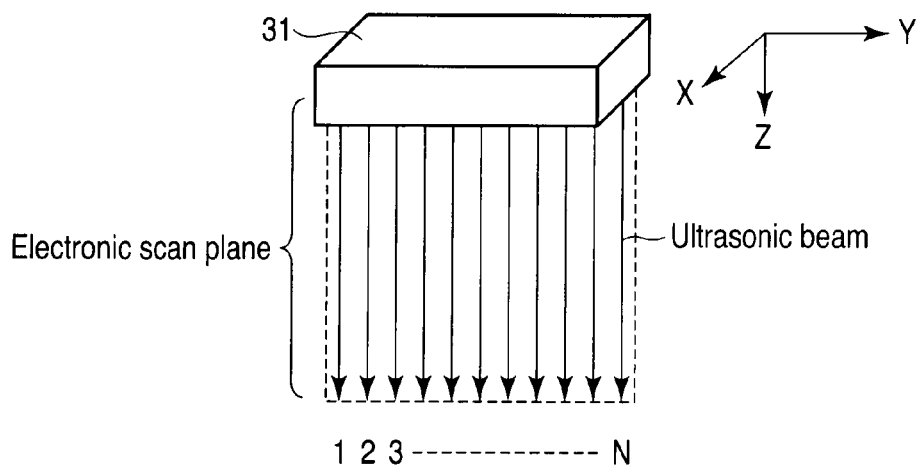
FIG. 2 is a view for explaining electronic scanning performed by a transmission unit and a reception unit in FIG. 1.

An embodiment of the present invention will be described below with reference to the views of the accompanying drawing.

FIG. 1 is a block diagram showing the arrangement of an ultrasonic diagnostic apparatus 1 according to this embodiment. As shown in FIG. 1, the ultrasonic diagnostic apparatus 1 comprises an ultrasonic diagnostic apparatus body 10 and a probe 30.

The ultrasonic diagnostic apparatus body 10 comprises a transmission unit 11, a reception unit 13, a scan line signal processing unit 15, an image generation unit 17, a display unit 19, a storage unit 21, a system control unit 23, an input unit 25, a movement control unit 27, and a position detection unit 29.

The probe 30 is connected to the ultrasonic diagnostic apparatus body 10, and comprises a transducer unit 31 and a moving mechanism 33. The function of each constituent element will be described below.

The transmission unit 11 includes a rate pulse generation circuit, delay circuit, driving pulse generation circuit, and the like (none of which are shown). The rate pulse generation circuit repeatedly generates rate pulses at a predetermined rate frequency fr Hz (period: 1/fr sec). The delay circuit gives each rate pulse a delay time necessary to focus an ultrasonic wave into a beam and determine transmission directivity for each channel. The driving pulse generation circuit generates ultrasonic driving pulses at the timings based on the respective delayed rate pulses. Upon receiving ultrasonic driving pulses, the transducers of the transducer unit 31 generate ultrasonic waves.

The transducer unit 31 includes a plurality of transducers, a backing member, an acoustic matching layer, and an acoustic lens (none of which are shown). The plurality of transducers are arrayed along one direction. Each transducer comprises a plurality of piezoelectric elements. The direction in which these transducers are arrayed will be referred to as the array direction. Each transducer receives a driving pulse applied from the transmission unit 11 and transmits an ultrasonic wave to a subject to be examined. Each transducer receives the ultrasonic wave reflected by the internal tissue of the subject or the like as an echo signal. The received echo signal is transmitted to the reception unit 13. The backing member is provided on the back surfaces of the plurality of transducers. The backing member suppresses vibrations and absorbs ultrasonic waves. The acoustic matching layer is provided on the front surfaces of the plurality of transducers. The acoustic matching layer is provided to suppress reflection of ultrasonic waves due to the differences in acoustic impedance between the subject and the plurality of transducers. The acoustic lens is provided on the front surface of the acoustic matching layer. The acoustic lens focuses ultrasonic waves in a direction different from the focusing direction of the delay circuit.

The reception unit 13 comprises a scan line signal generation unit 131 and a filter circuit 133.

The scan line signal generation unit 131 includes an amplifier circuit, analog-to-digital converter, delay circuit, and adder (not shown). The amplifier circuit amplifies echo signals from the subject for each channel. The analog-to-digital converter converts an amplified echo signal from an analog signal to a digital signal by sampling and quantizing the echo signal. The delay circuit gives each echo signal a delay time necessary to focus the echo signal converted into the digital signal in the form of a beam and sequentially change the reception directivity. The adder adds the echo signals to which the delay times are given.

With this addition, a reflection component from a direction corresponding to the reception directivity of the echo signal is enhanced to form a composite beam (ultrasonic beam) for ultrasonic transmission/reception in accordance with reception directivity and transmission directivity. The transmission unit 11 and the reception unit 13 control the transmission/reception of ultrasonic beams in this manner, thereby performing electronic scanning. One ultrasonic beam corresponds to one ultrasonic scan line. In this case, an echo signal for each ultrasonic scan line obtained by transmission/reception of an ultrasonic beam will be referred to as an actual measurement scan line signal. An actual measurement scan line signal is a set of echo signal components at sampling points set at predetermined intervals in the depth direction of an ultrasonic scan line at the time of sampling. In this case, "actual measurement" means being actually obtained by electronic scanning. All the ultrasonic scan lines in one electronic scan constitute one actual measurement electronic scan plane (frame). The storage unit 21 stores the data of a plurality of actual measurement scan line signals for each electronic scan plane.

FIG. 2 is a view for explaining electronic scanning controlled by the transmission unit 11 and the reception unit 13. As shown in FIG. 2, the Y-axis is defined as the array direction; the Z-axis is defined as the transmission/reception direction of an ultrasonic beam (the depth direction of an ultrasonic scan line); and the X-axis is defined as a direction perpendicular to the Y-Z plane. N lines extending from the transducer unit 31 along the Z-axis represent ultrasonic beams. Assume that a plane on which electronic scanning is actually performed (the plane enclosed with the dotted line in FIG. 2 (the Y-Z plane)) is an actual measurement electronic scan plane. The transmission unit 11 and the reception unit 13 cause the transducer unit 31 to transmit/receive first to Nth ultrasonic beams while sequentially changing their positions at time intervals dt, thereby performing electronic scanning. When the transmission/reception of the Nth ultrasonic beam finishes, transmission/reception of the first to Nth ultrasonic beams is repeated. In this manner, electronic scanning is repeated.

The filter circuit 133 is an electrical circuit having frequency selectivity. The filter circuit 133 allows a desired frequency component of an actual measurement scan line RF signal to pass therethrough and removes the remaining frequency components. After the filter processing, the actual measurement scan line signal is transmitted to the scan line signal processing unit 15.

Figure 3:
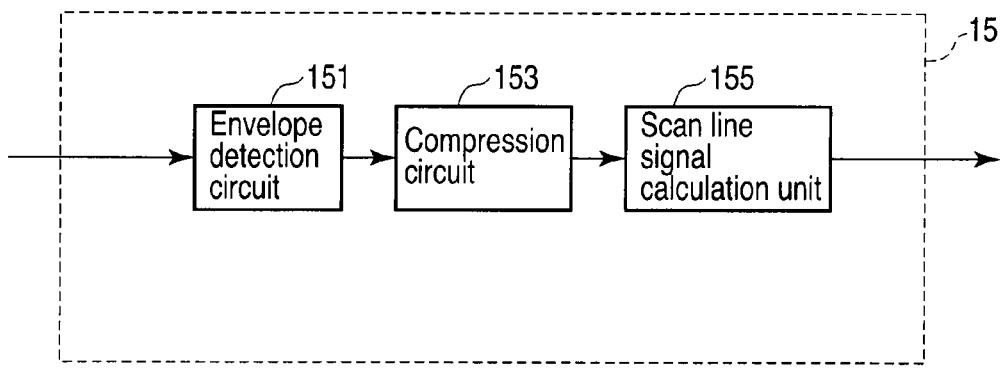
FIG. 3 is a block diagram showing the arrangement of an ultrasonic scan line signal processing unit in FIG. 1.

The scan line signal processing unit 15 performs various types of processing for actual measurement ultrasonic scan line signals from the reception unit 13. FIG. 3 is a block diagram showing the arrangement of the scan line signal processing unit 15. As shown in FIG. 3, the scan line signal processing unit 15 includes an envelope detection circuit 151, a compression circuit 153, and a scan line signal calculation unit 155.

The envelope detection circuit 151 performs envelope detection of an actual measurement scan line signal to detect the envelope of the actual measurement scan line signal.

The compression circuit 153 performs compression (or amplification) such as logarithmic compression of the envelope-detected actual measurement scan line signal. Note that the positions of the envelope detection circuit 151 and compression circuit 153 can be interchanged. That is, an actual measurement scan line signal can be compressed by the compression circuit 153 first, and can then be envelope-detected by the envelope detection circuit 151.

The scan line signal calculation unit 155 calculates a plurality of mathematical ultrasonic scan line signals constituting a plurality of mathematical electronic scan planes from a plurality of actual measurement ultrasonic scan line signals. In this case, "mathematical" means being obtained by calculation based on actual measurement ultrasonic scan line signals. Typically, the scan line signal calculation unit 155 calculates a plurality of mathematical scan line signals on the basis of the position of the transducer unit 31 which is detected by the position detection unit 29 (to be described later) such that a mathematical electron scan plane becomes perpendicular to the direction of movement of the transducer unit 31. However, a mathematical electronic scan plane need not always be perpendicular to the direction of movement and can be tilted. In addition, calculation processing for mathematical scan line signals is specifically interpolation or extrapolation. That is, the scan line signal calculation unit 155 interpolates or extrapolates a plurality of mathematical scan line signals on the basis of a plurality of actual measurement scan line signals. The plurality of mathematical ultrasonic scan line signals are transmitted to the image generation unit 17. The details of this calculation processing for ultrasonic scan line signals will be described later.

The image generation unit 17 generates multislice tomograms on the basis of a plurality of mathematical ultrasonic scan line signals. In addition, various types of pseudo-three-dimensional images such as maximum intensity projection images and surface images are generated by rendering a set of multislice tomograms, as needed.

The display unit 19 displays various types of images generated by the image generation unit 17.

An input unit 20 includes various switches, buttons, a trackball, a mouse, a keyboard, and the like which are used to input instructions from an operator, e.g., an instruction to stop scanning, the position of a mathematical electronic scan plane (to be described later), and the like to the ultrasonic diagnostic apparatus body 10.

A storage unit 18 stores a control program for executing ultrasonic scan line calculation processing, the data of scan line signals for each electronic scan plane, the position of the transducer unit 31, the positions of scan line signals, and the like.

The system control unit 23 has a function as an information processing apparatus (computer), and controls the operation of the ultrasonic diagnostic apparatus body 10. The system control unit 23 reads control programs for executing image generation, display, and the like from the storage unit 18, loads them into the memory which the unit has, and executes computation, control, and the like associated with the respective types of processing.

The moving mechanism 33 is a mechanism for moving the transducer unit 31 in a direction (direction of movement) crossing the array direction, and operates upon receiving the driving power of a motor. The slit plate of an optical or magnetic encoder is mounted on the rotating shaft of the motor of the moving mechanism 33. The encoder generates a pulse signal every time the rotating shaft of the motor rotates by a predetermined angle.

The position detection unit 29 counts the pulses of pulse signals from the encoder to specify the position of the transducer unit 31 from the count value. The position detection unit 29 can detect the reception position of a specific ultrasonic beam on the basis of the application timing of a driving pulse generated by the transmission unit 11 and a pulse signal from the encoder. Position detection processing will be described later.

The movement control unit 27 generates a driving signal for making the moving mechanism 33 operate on the basis of the detected position of the transducer unit 31 and the like, and supplies the generated driving signal to the moving mechanism 33. In this case, the movement control unit 27 controls the moving mechanism 33 to mechanically move the transducer unit 31 reciprocally and continuously (not intermittently) in the direction of movement (X-axis) at a proper timing and speed and in a proper position.

Figure 4:
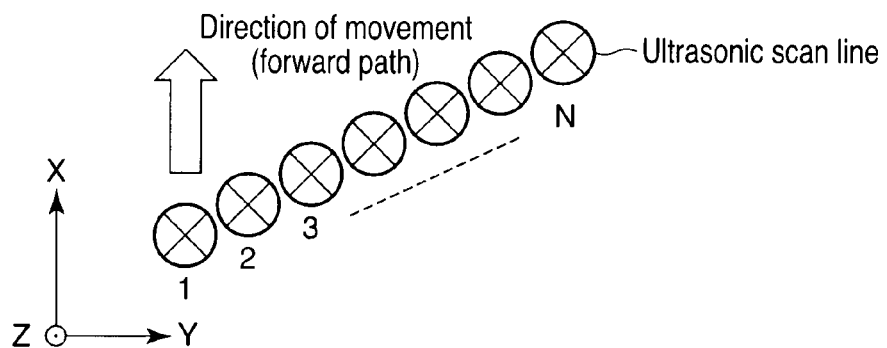
FIG. 4 is a view showing the positions of ultrasonic scan lines when a transducer unit in FIG. 1 moves along a forward path.
Figure 5:
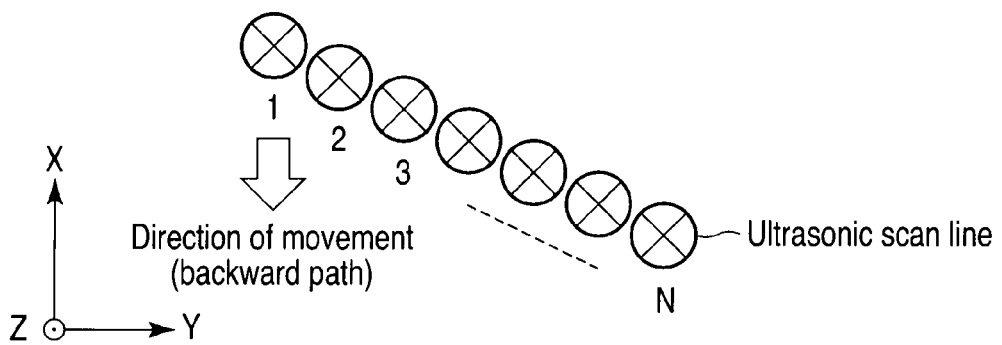
FIG. 5 is a view showing the positions of ultrasonic scan lines when the transducer unit in FIG. 1 moves along a backward path.

FIG. 4 is a view showing the positions of ultrasonic scan lines when the transducer unit 31 moves along a forward path. FIG. 5 is a view showing the positions of ultrasonic scan lines when the transducer unit 31 moves along a backward path. Assume that as shown in FIGS. 4 and 5, the transducer unit 31 moves in a direction (X-axis) perpendicular to the array direction (Y-axis). The circles shown in FIGS. 4 and 5 represent ultrasonic scan lines. The position of an ultrasonic scan line corresponds to the position of a scan line signal originating from the ultrasonic scan line. The movement control unit 27 continuously moves the transducer unit 31. During this movement, the transmission unit 11 and the reception unit 13 repeat electronic scanning (electronic/mechanical combination scanning). The actual measurement electronic scan plane comprising a plurality of ultrasonic scan line signals tilts with respect to the direction of movement (X-axis). As is obvious from the comparison between FIGS. 4 and 5, the tilting directions of the actual measurement electronic scan planes in the forward and backward paths differ from each other.

Calculation processing for mathematical scan line signals in this embodiment will be described next. Various calculation methods are available. For a concrete description of calculation processing, a method based on linear interpolation will be described below. A method of interpolating a mathematical ultrasonic scan line signal by using two actual measurement ultrasonic scan line signals will be described first.

Figure 6:
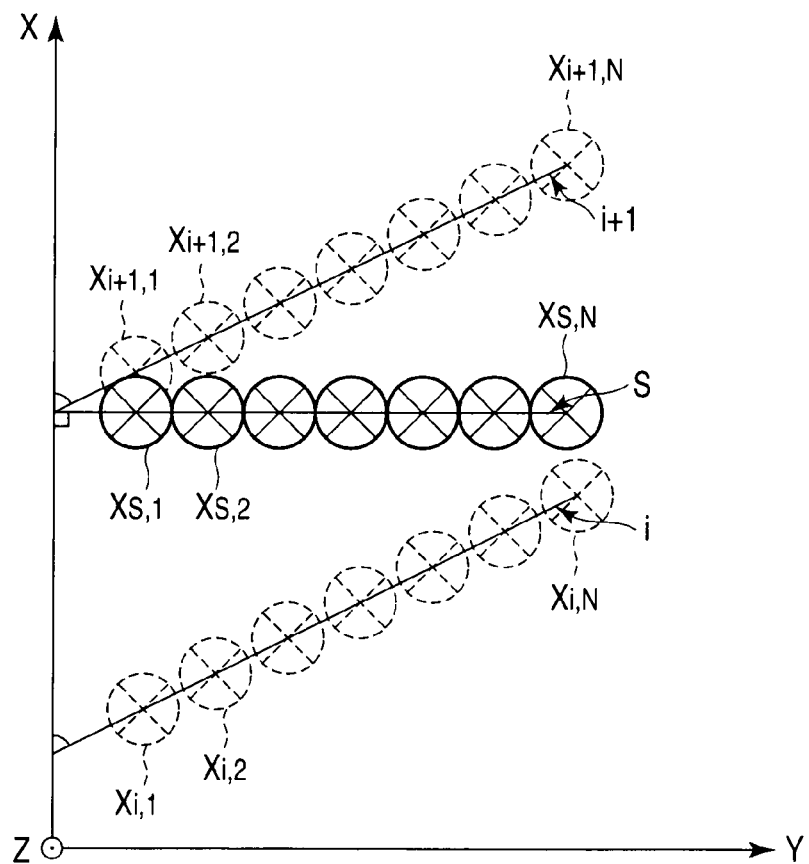
FIG. 6 is a view showing the positions of actual measurement electronic scan planes, actual measurement scan line signals, mathematical electronic scan plane, and mathematical scan line signal in a case in which the mathematical scan line signal is calculated by using the two actual measurement scan line signals in this embodiment and a modification of the embodiment.

FIG. 6 is a view showing the positional relationship between actual measurement electronic scan planes, actual measurement scan line signals, a mathematical electronic scan plane, and a mathematical scan line signal in a case in which a mathematical ultrasonic scan line signal is interpolated by using two actual measurement ultrasonic scan line signals. Each circle indicated by the dotted line represents a position X of an actual measurement scan line signal in the direction of movement (X-axis). Each circle indicated by the solid line represents a position X of a mathematical scan line signal X in the direction of movement (X-axis). The left subscript attached to the position X of each scan line signal represents an electronic scan plane number. The right subscript attached to each scan line signal X represents an ultrasonic scan line number corresponding to each scan line signal X. Note that the subscript "S" represents a mathematical electronic scan plane s. For example, a position $X_{i,1}$ of an ultrasonic scan line signal represents the position of the scan line signal associated with the first ultrasonic scan line on an actual measurement electronic scan plane i. According to another example, $X_{s,1}$ represents the position of a scan line signal associated with the first ultrasonic scan line on the mathematical electronic scan plane s. Positions $X_{s,1}$ to $X_{s,N}$ of a plurality of mathematical scan line signals constituting the same mathematical electronic scan plane s are the same.

The system control unit 23 determines the position of the mathematical electronic scan plane s. The system control unit 23 determines the positions of a plurality of mathematical ultrasonic scan line signals such that a plurality of mathematical electronic scan planes are perpendicular to the direction of movement and parallel to each other. For example, as shown in FIG. 6, the position of the mathematical electronic scan plane s perpendicular to the direction of movement is located between the positions of actual measurement electronic scan planes i and i+1 which are adjacent to each other.

Figure 7:
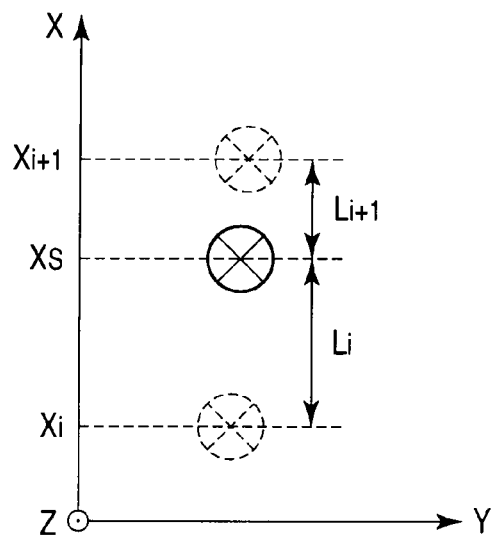
FIG. 7 is a view showing the distances between two actual measurement scan line signals and a mathematical scan line signal in a case in which the mathematical scan line signal is calculated by using the two actual measurement scan line signals in this embodiment and a modification of the embodiment.

FIG. 7 is a view showing the distances between two actual measurement scan line signals and a mathematical scan line signal in a case in which the mathematical scan line signal is interpolated by using the two actual measurement scan line signals. For the sake of convenience, FIG. 7 shows each one of scan line signals, of a plurality of scan line signals constituting electronic scan planes, which have the same ultrasonic scan line numbers, for each electronic scan plane. That is, $X_i$ represents the position of an ultrasonic scan line signal at a desired ultrasonic scan line number on the electronic scan plane i; $X_{i+1}$, the position of a scan line signal associated with an ultrasonic scan line with the same number as $X_i$ on the electronic scan plane i+1; and $X_s$, the position of a scan line signal associated with an ultrasonic scan line with the same number as $X_i$ on the electronic scan plane s. $L_i$ represents the distance between the position $X_s$ of the scan line signal and the position $X_i$ of the scan line signal; and $L_{i+1}$, the distance between the position $X_{i+1}$ of the scan line signal and the position $X_s$ of a scan line signal $S_s$. As is obvious from FIGS. 6 and 7, the distances $L_i$ and $L_{i+1}$ change in accordance with the positions (numbers) of ultrasonic scan lines. A method of detecting the position of each scan line signal will be described later.

Reference symbols $S_i$, $S_{i+1}$, and $S_s$ respectively denote scan line signals corresponding to the positions $X_i$, $X_{i+1}$, and $X_s$. When a mathematical scan line signal is to be calculated by using two actual measurement scan line signals $S_i$ and $S_{i+1}$, the scan line signal calculation unit 155 calculates (interpolates) the mathematical ultrasonic scan line signal $S_s$ for each ultrasonic scan line by applying the two actual measurement scan line signals $S_i$ and $S_{i+1}$ to linear interpolation expression (1) given below:

$$S_s = (L_i \cdot S_i + L_{i+1} \cdot S_{i+1})/(L_i + L_{i+1}) \tag{1}$$

As described above, the actual measurement ultrasonic scan line signals $S_i$ and $S_{i+1}$ are sets of echo signal components at sampling points in the depth direction (Z-axis) of an ultrasonic scan line. The scan line signal calculation unit 155 therefore calculates echo signal components, of the two actual measurement scan line signals $S_i$ and $S_{i+1}$, which are obtained at sampling points at the same position by using expression (1). The scan line signal calculation unit 155 calculates echo signal components at all the sampling points of the two actual measurement scan line signals $S_i$ and $S_{i+1}$ associated with a given ultrasonic scan line, thereby calculating the mathematical ultrasonic scan line signal $S_s$ associated with the ultrasonic scan line.

A method of interpolating a mathematical scan line signal by using three actual measurement scan line signals will be described next.

Figure 8:
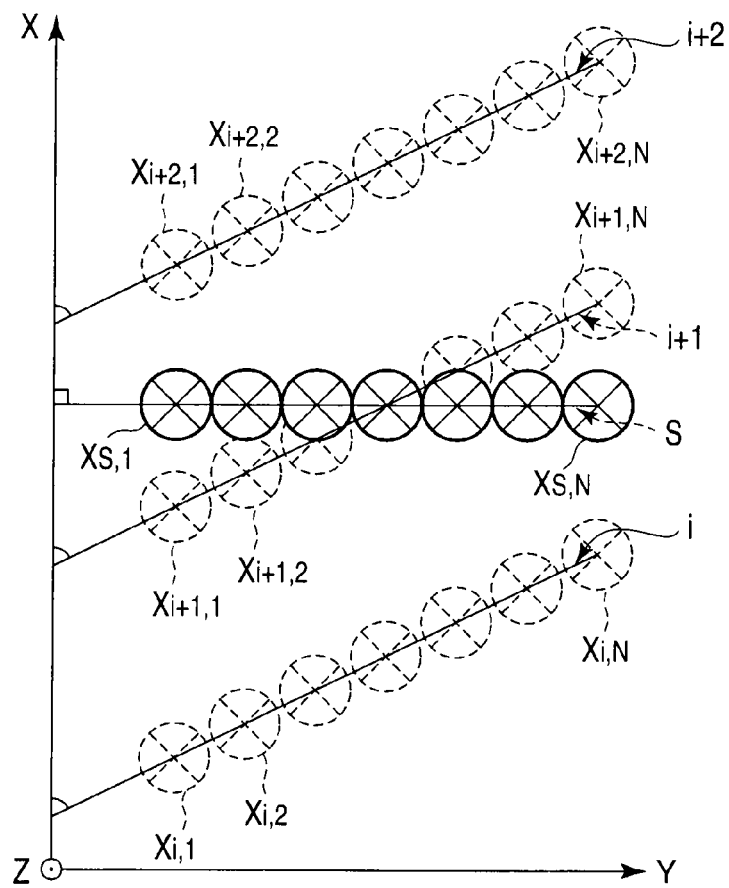
FIG. 8 is a view showing the positions of actual measurement electronic scan planes, actual measurement scan line signals, mathematical electronic scan plane, and mathematical scan line signal in a case in which a mathematical scan line signal is calculated by using three actual measurement scan line signals in this embodiment and a modification of the embodiment.

FIG. 8 is a view showing the positional relationship between actual measurement electronic scan planes, actual measurement scan line signals, a mathematical electronic scan plane, and a mathematical scan line signal in a case in which the mathematical scan line signal is interpolated by using the three actual measurement scan line signals. As in FIG. 6, the circles indicated by the dotted lines represent positions $X_{i,1}$ to $X_{i,N}$, $X_{i+1,1}$ to $X_{i+1,N}$, and $X_{i+2,1}$ to $X_{i+2,N}$ of actual measurement scan line signals $S_{i,1}$ to $S_{i,N}$, $S_{i+1,1}$ to $S_{i+1,N}$, and $S_{i+2,1}$ to $S_{i+2,N}$, and the circles indicated by the solid lines represent positions $X_{s,1}$ to $X_{s,N}$ of mathematical scan line signals $S_{s,1}$ to $S_{s,N}$. As shown in FIG. 8, the position of the mathematical electronic scan plane s perpendicular to the direction of movement is located between the positions of the electronic scan planes i and i+2, of the three consecutive actual measurement electronic scan planes i, i+1, and i+2, which are located on the two ends.

Figure 9:
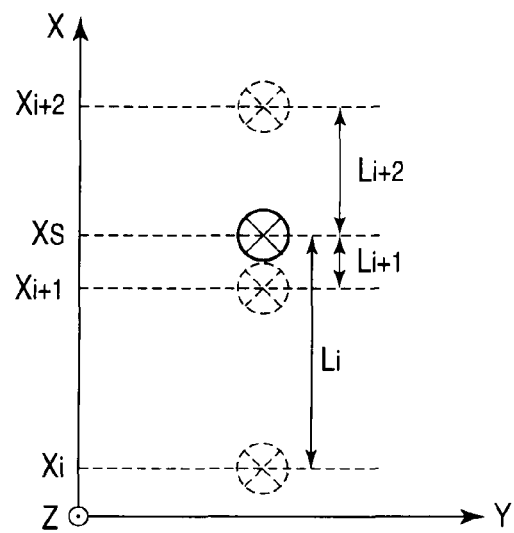
FIG. 9 is a view showing the distances between three actual measurement scan line signals and a mathematical scan line signal in a case in which the mathematical scan line signal is calculated by using the three actual measurement scan line signals in this embodiment and a modification of the embodiment.

FIG. 9 is a view showing the distances between the positions of the three actual measurement scan line signals $S_{i,1}$ to $S_{i,N}$, $S_{i+1,1}$ to $S_{i+1,N}$, and $S_{i+2,1}$ to $S_{i+2,N}$ and the position of one signal of the mathematical scan line signals $S_{s,1}$ to $S_{s,N}$ in a case in which the mathematical scan line signal is interpolated by using the three actual measurement scan line signals. As shown in FIG. 9, $L_{i+2}$ represents the distance between the position $X_{i+2}$ of the scan line signal $S_{i+2}$ and the position $X_s$ of the scan line signal $S_s$. Like the distances $L_i$ and $L_{i+1}$, this distance changes depending on the position (number) of an ultrasonic scan line.

The scan line signal calculation unit 155 interpolates the mathematical scan line signal $S_s$ for each ultrasonic scan line by applying the three actual measurement scan line signals $S_i$, $S_{i+1}$, and $S_{i+2}$ to linear interpolation expression (2) given below:

$$S_s = \{L_i(S_{i+1}+S_{i+2}) + L_{i+1}(S_{i+2}-S_i) + L_{i+2}(S_i+S_{i+1})\}/(L_i+L_{i+2}) \tag{2}$$

The scan line signal calculation unit 155 calculates a plurality of mathematical scan line signals $S_{s,1}$ to $S_{s,N}$ corresponding to a plurality of mathematical electronic scan planes by using expression (1) or (2) given above. The image generation unit 17 generates multislice tomograms perpendicular to the direction of movement (X-axis) on the basis of the plurality of mathematical scan line signals $S_{s,1}$ to $S_{s,N}$. The image generation unit 17 generates various pseudo-three-dimensional images by performing rendering processing for the multislice tomograms perpendicular to the direction of movement. This rendering processing is performed for the multislice tomograms perpendicular to the direction of movement (X-axis), and hence does not require any complicated computation such as coordinate transformation for making slices perpendicular to the direction of movement (X-axis). That is, this processing is very simple processing. The resultant pseudo-three-dimensional images do not require any complicated computation such as coordinate transformation, and hence are high-resolution, high-quality images.

When the system control unit 23 determines the positions $X_{s,1}$ to $X_{s,N}$ of a plurality of mathematical scan line signals such that a plurality of mathematical electronic scan planes are arranged at predetermined intervals (along the X-axis), the image generation unit 17 generates multislice tomograms having uniform intervals along the direction of movement (X-axis) of the transducer unit 31. A pseudo-three-dimensional image based on multislice tomograms having uniform intervals is higher in resolution than a pseudo-three-dimensional image based on multislice tomograms having random intervals.

The above description has exemplified the case in which electronic scanning is performed while the transducer unit 31 is moved in one direction. The following is a case in which electronic scanning is performed while the transducer unit 31 is moved reciprocally.

Figure 10:
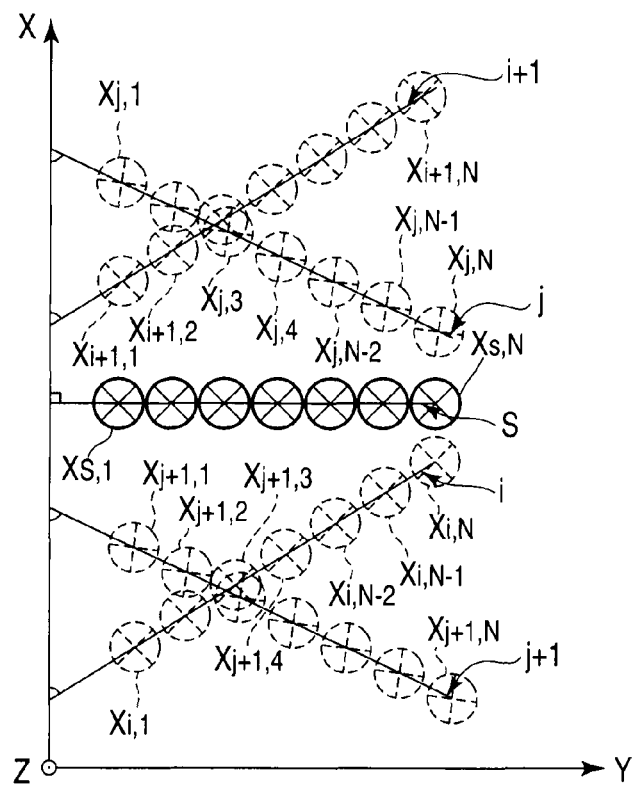
FIG. 10 is a view showing the positions of electronic scan planes, scan line signals, mathematical electronic scan plane, and mathematical scan line signal in a case in which the transducer unit in FIG. 1 moves reciprocally.

FIG. 10 is a view showing the positional relationship between actual measurement electronic scan planes, actual measurement scan line signals, a mathematical electronic scan plane, and a mathematical scan line signal in a case in which the transducer unit 31 is moved reciprocally. Assume that as shown in FIG. 10, "i" is the subscript of the position X of a scan line signal associated with a forward path, and "j" is the subscript of the position X of a scan line signal associated with a backward path. The scan line signal calculation unit 155 interpolates mathematical scan line signals $S_{s,1}$ to $S_{s,N}$ constituting a mathematical scan line plane s perpendicular to the direction of movement (X-axis) by applying a plurality of scan line signals $S_{i,1}$ to $S_{i,N}$, $S_{i+1,1}$ to $S_{i+1,N}$, $S_{j,1}$ to $S_{j,N}$, and $S_{j+1,1}$ to $S_{j+1,N}$ constituting an electronic scan plane i in a forward path and an electronic scan plane j in a backward path to expression (1) or (2).

The image generation unit 17 can generate a pseudo-three-dimensional image by simple rendering processing without any consideration to the differences between the positions and angles of actual measurement electronic scan planes in forward and backward paths of the transducer unit 31 on the basis of the plurality of mathematical scan line scan line signals $S_{s,1}$ to $S_{s,N}$ calculated by the above method. The simple rendering processing allows the image generation unit 17 to generate a pseudo-three-dimensional image in real time while the transducer unit 31 continuously moves reciprocally. The display unit 19 can display the pseudo-three-dimensional image in real time.

The following method is available as a method of calculating a mathematical scan line signal on the basis of actual measurement scan line signals in forward and backward paths. The scan line signal calculation unit 155 calculates mathematical scan line signals $S_{s,1}$ to $S_{s,N}$ by applying to expression (1) or (2) or the like scan line signals (scan line signals corresponding to the positions $X_{i+1,1}$, $X_{j+1,1}$, $X_{i+1,2}$, $X_{j+1,2}$, $X_{j,3}$, $X_{i,3}$, $X_{j,4}$, $X_{i,4}$, $X_{j,N-2}$, $X_{i,N-2}$, $X_{j,N-1}$, $X_{i,N-1}$, $X_{j,N}$, and $X_{i,N}$ FIG. 10), of the scan line signals in forward and backward paths, which are close to mathematical scan line signals $S_{s,1}$ to $S_{s,N}$ and located on the two sides thereof. As a result, a tomogram is generated on the basis of the actual measurement scan line signals obtained at positions closer to the mathematical scan line signal. When the subject is at rest, therefore, the image generation unit 17 can generate a tomogram higher in resolution than a tomogram associated with only a forward or backward path.

If the moving speed of the transducer unit 31 is high, the density of ultrasonic scan lines in the electronic scanning direction and the density of electronic scan planes in the direction of movement increase. In this case, the system control unit 23 sets the parameter $X_s$ to several values. The scan line signal calculation unit 155 then calculates a plurality of mathematical scan line signals by properly combining linear interpolation expressions such as expressions (1) and (2). As a consequence, the number of mathematical electronic scan planes s becomes large relative to the numbers of actual measurement electronic scan planes i and j and the like. This allows the image generation unit 17 to generate a more uniform pseudo-three-dimensional image.

Note that the above scan line signal calculation processing is all performed by using a linear interpolation expression such as expression (1) or (2). However, the present invention is not limited to this, and scan line signal calculation processing can be performed by using a high-order interpolation expression such as a spline function or a SINC function. Alternatively, scan line signal calculation processing can be performed by using an extrapolation method using a linear function, a spline function, or a SINC function.

A method of detecting the positions of scan line signals will be described next. There are mainly three methods of detecting the position of each scan line signal.

The first method will be described first. First of all, the position detection unit 29 specifies the position of the transducer unit 31 at the time of reception of an ultrasonic beam, which is a reference position (number) in each electronic scan. Assume that in the following description, a reference position (number) is the first position. The position of the transducer unit 31 at the time of reception of the first ultrasonic beam is almost the same as the position of, for example, the scan line signal $S_{i,1}$ or $S_{i+1,1}$ which is associated with the first ultrasonic line on each electronic scan plane. Since time intervals dt of ultrasonic beam transmission/reception are constant, the position detection unit 29 calculates the positions of scan line signals $S_{i,2}$ to $S_{i,N}$ and $S_{i+1,2}$ to $S_{i+1,N}$ and the like associated with all the ultrasonic scan lines on the basis of the positions of the scan line signals $S_{i,1}$ and $S_{i+1,1}$ and the like associated with the first ultrasonic scan line and the time intervals from the reception time of the first ultrasonic beam.

The second method will be described next. When the movement control unit 27 continuously moves the transducer unit 31 at a constant speed and ultrasonic beams are transmitted/received at predetermined constant intervals dt, the position detection unit 29 approximately calculates the positions of all the scan line signals $S_{i,1}$ to $S_{i,N}$ and $S_{i+1,1}$ to $S_{i+1,N}$ and the like from the time when the continuous movement is started.

The third method will be described next. The position detection unit 29 detects (actually measures) the positions of all the scan line signals $S_{i,1}$ to $S_{i,N}$ and $S_{i+1,1}$ to $S_{i+1,N}$ and the like on the basis of the time of reception of each ultrasonic beam and the position of the transducer unit 31. This method can obtain high-resolution tomograms as compared with the other two methods. In this case, the scan line signal calculation unit 155 coherently calculates scan line signals by using an aperture synthesis technique. This allows the image generation unit 17 to improve the resolution of a pseudo-three-dimensional image associated with the direction of movement.

In the above manner, this embodiment can easily generate a high-resolution, high-quality pseudo-three-dimensional image while implementing high-speed 3D scanning which performs electronic scanning while mechanically and continuously moving the transducer unit.

(Modification of Embodiment)

A modification of this embodiment exemplifies an ultrasonic diagnostic apparatus which calculates a plurality of mathematical scan line signals on the basis of a plurality of actual measurement scan line signals before envelope detection. Note that the same reference numerals denote constituent elements having substantially the same functions as in this embodiment, and a repetitive description will be made only when required.

Figure 11:
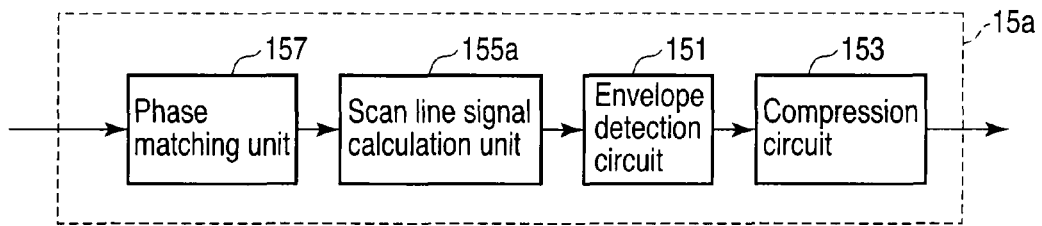
FIG. 11 is a block diagram showing the arrangement of a first scan line signal processing unit in a modification of this embodiment.

FIG. 11 is a block diagram showing the arrangement of a scan line signal processing unit 15a according to a modification of this embodiment. As shown in FIG. 11, the scan line signal processing unit 15a includes a phase matching unit 157, the scan line signal calculation unit 155a, the envelope detection circuit 151, and the compression circuit 153.

The phase matching unit 157 matches the phases of a plurality of actual measurement scan line signals on the same ultrasonic scan line.

Figure 12:
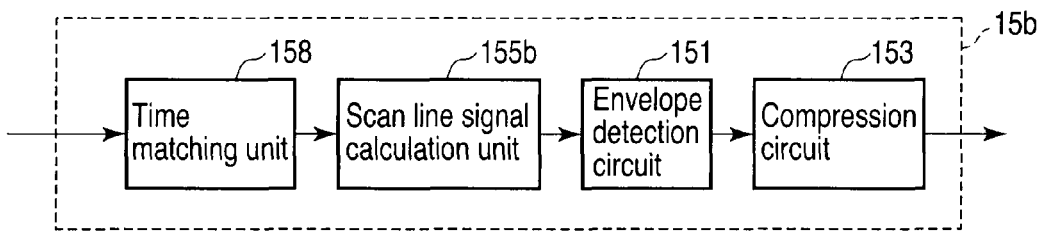
FIG. 12 is a block diagram showing the arrangement of a second scan line signal processing unit in a modification of this embodiment.
Figure 13:
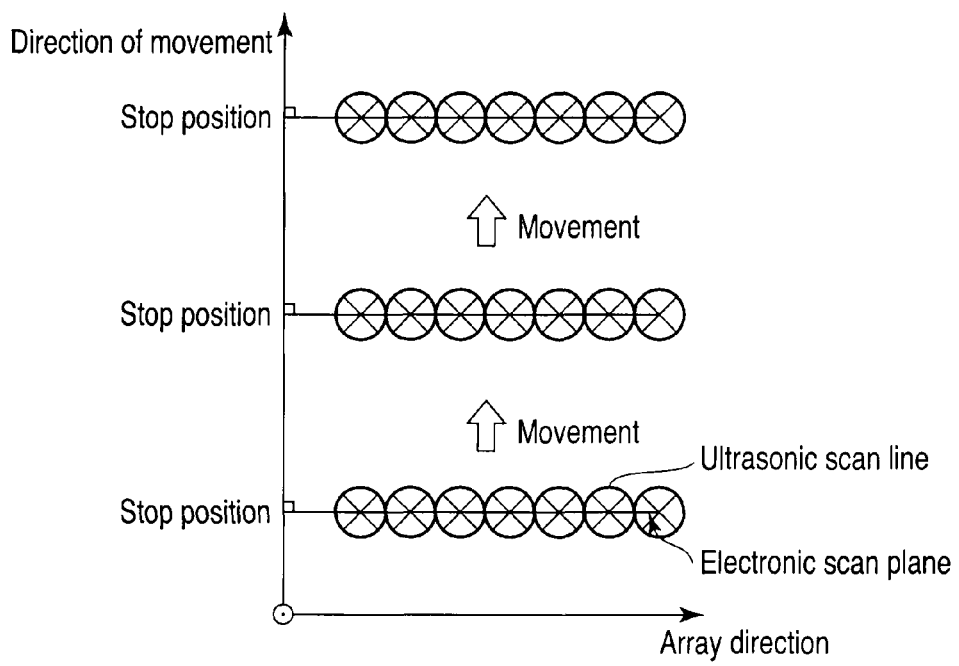
FIG. 13 is a view showing the positional relationship between electronic scan planes, ultrasonic scan lines, and the direction of movement in a case in which electronic scanning is performed while a transducer unit is intermittently moved according to the prior art.

As shown in FIG. 12, a scan line signal processing unit 15b may include a time matching unit 158 in place of the phase matching unit 157. The time matching unit 158 matches the times of a plurality of scan line signals on the same ultrasonic scan line.

If there is no need to perform phase matching or time matching, the scan line signal processing unit 15a need not have the phase matching unit 157, and the scan line signal processing unit 15b need not have the time matching unit 158.

Scan line signal calculation units 155a and 155b calculate at least two mathematical scan line signals constituting a mathematical electronic scan plane perpendicular to the direction of movement from a plurality of actual measurement scan line signals constituting at least two actual measurement electronic scan planes on the basis of the detected position of the transducer unit 31. The storage unit 21 stores the data of a plurality of mathematical scan line signals for each electronic scan plane.

The envelope detection circuit 151 performs envelope detection of a mathematical scan line signal to detect the envelope of the mathematical scan line signal.

The compression circuit 153 performs compression (or amplification) such as logarithmic compression (or logarithmic amplification) of the envelope-detected mathematical scan line signal. Note that the positions of the envelope detection circuit 151 and compression circuit 153 can be interchanged.

Mathematical scan line signal calculation processing in a modification of this embodiment will be described next. The positions of actual measurement scan line signals, actual measurement electronic scan planes, mathematical scan line signals, and mathematical electronic scan planes are the same as those shown in FIGS. 6 and 8.

The distances between the actual measurement scan line signals $S_{i,1}$ to $S_{i,N}$, $S_{i+1,1}$ to $S_{i+1,N}$, and $S_{i+2,1}$ to $S_{i+2,N}$ and the mathematical scan line signals $S_{s,1}$ to $S_{s,N}$ are the same as the distances $L_i$, $L_{i+1}$, and $L_{i+2}$.

The scan line signal calculation units 155a and 155b calculate a plurality of mathematical scan line signals constituting an electronic scan plane perpendicular to the direction of movement by applying a plurality of actual measurement scan line signals to, for example, expression (1) or (2).

When the scan line signal calculation units 155a and 155b calculate the mathematical ultrasonic scan line signals $S_{s,1}$ to $S_{s,N}$ for all the ultrasonic scan lines, the mathematical electronic scan plane s perpendicular to the direction of movement is formed. In this case, the scan line signal calculation units 155a and 155b calculate echo signal components, of the echo signal components of the actual measurement scan line signal $S_{i,Si+1}$, which are located at the same sampling point, by using expression (1) or (2). When the scan line signal calculation units 155a and 155b calculate echo signal components at all the sampling points of the actual measurement scan line signals $S_i$ and $S_{i+1}$ associated with a given one ultrasonic scan line, the mathematical ultrasonic scan line signal $S_s$ associated with the ultrasonic scan line is calculated. The data of the plurality of mathematical scan line signals $S_{s,1}$ to $S_{s,N}$ are stored in the storage unit 21 for each electronic scan plane.

The envelope detection circuit 151 performs envelope detection of the calculated mathematical scan line signals $S_{s,1}$ to $S_{s,N}$. The compression circuit 153 compresses the signals. The image generation unit 17 generates multislice tomograms on the basis of the plurality of mathematical scan line signals. The image generation unit 17 then generates various pseudo-three-dimensional images by rendering a set of multislice tomograms perpendicular to the direction of movement. The display unit 19 displays the generated various images.

Note that the scan line processing units 15a and 15b comprise quadrature detection circuits (not shown) for extracting Doppler signals of scan line signals. The scan line signal calculation units 155a and 155b can calculate mathematical scan line signals on the basis of a plurality of quadrature-detected actual measurement scan line signals.

The modification of this embodiment can therefore easily generate a high-resolution, high-quality pseudo-three-dimensional image while implementing high-speed 3D scanning which performs electronic scanning while mechanically and continuously moving the transducer unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
a probe including a transducer unit including a plurality of transducers which are arrayed in a first direction, transmit ultrasonic waves and receive echo signals, and a moving mechanism for continuously moving the transducer unit in a second direction crossing the first direction;
a control unit which controls the moving mechanism to continuously move the transducer unit in the second direction;
a transmission unit which causes the transducer unit to generate ultrasonic waves;

a signal generation unit which generates a plurality of actual measurement scan line signals by delaying and adding a plurality of echo signals from the transducer unit;

a detection unit which detects positions of the plurality of actual measurement scan line signals;

a determination unit which determines positions of a plurality of mathematical scan line signals regarding a plurality of mathematical electronic scan planes based on the positions of the plurality of actual measurement scan line signals;

a signal calculation unit which calculates a plurality of mathematical scan line signals from the plurality of actual measurement scan line signals based on distances between the detected positions of the plurality of actual measurement scan line signals and the determined positions of the plurality of mathematical scan line signals; and an image generation unit which generates multislice tomograms on the basis of the plurality of calculated mathematical scan line signals.

2. The apparatus according to claim 1, wherein the signal calculation unit interpolates the plurality of mathematical scan line signals from the plurality of actual measurement scan line signals.

3. The apparatus according to claim 1,
wherein the mathematical electronic scan planes are arranged between a plurality of actual electronic scan planes adjacent to each other in the second direction.

4. The apparatus according to claim 1, which further comprises a detection circuit which performs detection processing of the plurality of actual measurement scan line signals, and in which
the signal calculation unit calculates a plurality of mathematical ultrasonic scan line signals from a plurality of actual measurement scan line signals having undergone the detection processing on the basis of the detected position of the transducer unit.

5. The apparatus according to claim 4, wherein the detection circuit performs envelope detection processing as the detection processing.

6. The apparatus according to claim 4, wherein the detection circuit performs quadrature detection processing as the detection processing.

7. The apparatus according to claim 1, further comprising a phase matching unit which matches phases of the plurality of actual measurement scan line signals in accordance with a position of the scan line signal.

8. The apparatus according to claim 1, further comprising a time matching unit which matches times of the plurality of actual measurement scan line signals in accordance with a position of the scan line signal.

9. The apparatus according to claim 1, wherein the signal calculation unit calculates the plurality of mathematical scan line signals such that the plurality of mathematical electronic scan planes are arranged at equal intervals.

10. The apparatus according to claim 1, wherein the signal calculation unit calculates the plurality of mathematical scan line signals such that a position of the mathematical electronic scan plane in a forward path substantially coincides with a position of the mathematical electronic scan plane in a backward path with respect to movement of the transducer unit in the second direction.

11. The apparatus according to claim 1, wherein the signal calculation unit calculates the plurality of mathematical scan line signals such that the mathematical electronic scan planes become larger in number than the actual measurement electronic scan planes.

12. The apparatus according to claim 1, wherein the signal calculation unit calculates a plurality of mathematical scan line signals constituting a mathematical electronic scan plane perpendicular to the second direction on the basis of the plurality of actual measurement scan line signals constituting the actual measurement electronic scan plane in a forward path and the plurality of actual measurement scan line signals constituting the actual measurement electronic scan plane in a backward path with respect to movement of the transducer unit along the second direction.

13. The apparatus according to claim 1, wherein the image generation unit generates a pseudo-three dimensional image by rendering a set of the multislice tomograms.

14. The apparatus according to claim 1, wherein the plurality of mathematical electronic scan planes are perpendicular to the second direction.

15. An ultrasonic diagnostic apparatus comprising:
a storage unit which stores a plurality of actual measurement scan line signals constituting a plurality of actual measurement electronic scan planes;

a determination unit which determines positions of a plurality of mathematical scan line signals regarding a plurality of mathematical electronic scan planes perpendicular to a moving direction of an ultrasonic probe;

a signal calculation unit which calculates a plurality of mathematical scan line signals from the plurality of actual measurement scan line signals based on distances between positions of the plurality of actual measurement scan line signals and positions of the plurality of mathematical scan line signals; and an image generation unit which generates multislice tomograms on the basis of the plurality of calculated mathematical scan line signals.

\* \* \* \* \*